United States Patent
Rossmeier et al.

(10) Patent No.: US 8,595,027 B2
(45) Date of Patent: Nov. 26, 2013

(54) LAYERS IN THE APPOINTMENT BOOK

(75) Inventors: Markus Rossmeier, Bamberg (DE); Beate Schwichtenberg, Münich (DE)

(73) Assignee: Siemens Aktiengesellschaft, Munich (DE)

( * ) Notice: Subject to any disclaimer, the term of this patent is extended or adjusted under 35 U.S.C. 154(b) by 542 days.

(21) Appl. No.: 12/285,921

(22) Filed: Oct. 16, 2008

(65) Prior Publication Data
US 2009/0106048 A1 Apr. 23, 2009

(30) Foreign Application Priority Data
Oct. 19, 2007 (DE) .......................... 10 2007 050 182

(51) Int. Cl.
*G06Q 10/00* (2012.01)

(52) U.S. Cl.
USPC .................................................. 705/2; 705/3

(58) Field of Classification Search
USPC .......................................................... 705/2
See application file for complete search history.

(56) References Cited

U.S. PATENT DOCUMENTS

| 2005/0004815 A1* | 1/2005 | Machtelinck | 705/2 |
| 2006/0173713 A1* | 8/2006 | Petro et al. | 705/2 |
| 2006/0195484 A1* | 8/2006 | Mahesh et al. | 707/200 |

FOREIGN PATENT DOCUMENTS

| DE | 10114017 A1 | 9/2001 |
| DE | 10319085 B4 | 9/2005 |
| EP | 1515259 A1 | 3/2005 |

* cited by examiner

*Primary Examiner* — Hiep V Nguyen
(74) *Attorney, Agent, or Firm* — Harness, Dickey & Pierce, P.L.C.

(57) ABSTRACT

A method and a scheduling system are disclosed for processing medical scheduling data which relates to the job planning for a medical appliance and of which each scheduling data item is associated with a data level. In at least one embodiment of the method a data level association is determined for each scheduling data item to be displayed, wherein the data level association relates to the data level associated with the scheduling data item, the data level or data levels currently to be displayed are ascertained, the data level association of the scheduling data item to be displayed is compared with the data level or data levels which are currently to be displayed, and the scheduling data item to be displayed is displayed if the data level association corresponds to at least one data level which is currently to be displayed.

20 Claims, 2 Drawing Sheets

LAYERS IN THE APPOINTMENT BOOK

PRIORITY STATEMENT

The present application hereby claims priority under 35 U.S.C. §119 on German patent application number DE 10 2007 050 182.1 filed Oct. 19, 2007, the entire contents of which is hereby incorporated herein by reference.

FIELD

Embodiments of the invention generally relate to an area in the health service and/or generally relate to a method for processing medical scheduling data and/or to a medical scheduling system.

BACKGROUND

Great expectations are placed on the appointments management in radiology. For example, the appointments management needs to support a plurality of appliances, needs to be clear and needs to permit changes.

The appointments management should provide for the allocated appointments to be visible so that a user can tell at a glance where there are still gaps which can be filled with new appointments.

The appointments management should also be able to support the allocation of appointments by taking into account the presence and absence of various doctors, other internal appointments, appliance preparation for specific examinations, the functions available on the appliance, etc.

The desire for optimum workload and an optimum order for the examinations in order to minimize appliance conversion times or avoid the cleaning time for contagious patients likewise determines the requirements that are placed on the appointments management.

Further requirements are the comprehensibility of changes in the appointments allocation, e.g. in the event of last-minute appointment cancellations or nonattendance by the patient, and a comparison of the scheduled sequence of appointments with the actual sequence of appointments on the appliance. This is used not only for the purposes of control by the radiology management, but rather is needed on the date of the appointment in order to incorporate emergencies into the sequence, and for information for patients (waiting time).

In a piece of appointments management software or a scheduling system, various tasks are performed by various people:
- examination planning/workload planning—e.g. radiology management
- general allocation of appointments—e.g. telephone service/allocation of appointments
- control of workload—e.g. radiology management
- information for patients/allocation of appointments for emergencies—e.g. reception In this case, the following problem needs to be solved: A limited space (for example a normal monitor) is intended to be able to be used to implement the tasks described above taking account of all the necessary supporting information.

In many places today, it is customary for appointments management to be in a paper appointment book into which the presence and absence of different doctors are entered. The scheduled and actual sequences of appointments can be compared only by way of a telephone query.

SUMMARY

In at least one embodiment the present invention, a way is shown in which ordered and clear scheduling or appointments allocation is possible. The user is intended to be provided with a display presenting the data which are relevant to him in a particular situation. When the user creates new scheduling data, it is necessary to ensure that the new scheduling data are stored in an orderly manner.

Embodiments of the invention will be explained below with reference to the solution based on the method. Advantages, features or alternative embodiments mentioned in this context can accordingly also be transferred to the other solutions of the invention. Accordingly, the device for searching and the hospital information system and the health-telematics system can also be developed by features which are mentioned in connection with the description of the method or features from the subclaims relating to the method.

First of all, it should be noted at this juncture that the solution based on at least one embodiment of the invention is, in principle, not limited to the order in which the method steps are listed in the method claims. Although the order of listing in the example embodiment matches the order in which the steps are performed, it is likewise possible, in alternative embodiments, for individual method steps to be performed in parallel or with timing overlaps.

One example embodiment involves a method for processing medical scheduling data which relates to the job planning for a medical appliance and of which each scheduling data item is associated with a data level, having the following method steps:
a data level association is determined for each scheduling data item to be displayed, wherein the data level association relates to the data level associated with the scheduling data item,
the data level currently to be displayed is ascertained,
the level association of the scheduling data item to be displayed is compared with the data level or data levels which is/are currently to be displayed,
the scheduling data item to be displayed is displayed if the level association corresponds to at least one data level which is currently to be displayed.

To improve understanding, a few terms in the method are defined below.

"Medical scheduling data" are to be understood to mean data which are used as part of the job planning for a medical appliance. These may firstly be data which define appointments which are used to stipulate at what times a particular medical appliance is being used by whom. In this case, a scheduling data item defines a chronologically determinant start, a chronologically determinant end, the medical appliance in question, and a description for the scheduling data item. In addition, the scheduling data item may also contain statements relating to the patient and to the operator. Furthermore, the term medical scheduling data also covers data which provides additional information for the job planning. This additional information may define, by way of example, restrictions for the allocation of appointments for a particular period (for example: "13.3., 8:00-13:00 Prof. XYZ not in the building". This information relates to all appliances for which Prof XYZ is responsible, and restricts the use of these appliances). The term medical scheduling data also covers information which determines the type of display and the organization of appointments, such as a time frame.

The aim of job planning is to use the available medical appliances as efficiently as possible. This means that appointment clashes, relatively long waiting times and, as far as possible, idle phases need to be avoided.

The data levels structure and order the scheduling data, which belong to different types or categories. A scheduling data item is usually associated with one data level. To associate a scheduling data item with the data level, a data level association is provided for each scheduling data item.

When the scheduling data need to be displayed, they are filtered using the data level association, inter alia. In this case, the filter criterion used is a currently displayed data level or the combination of a plurality of currently displayed data levels. The currently displayed data level(s) can be selected by the user, so that the user obtains a display of the data levels which are currently of interest to him. The display of the scheduling data is therefore clear and the user can quickly obtain a picture of the current job planning for the different medical appliances.

The levels can be presented selectively by a level manager. By displaying and hiding levels, it is possible to selectively display contents which are required for the current activity. The levels define the priority of the presentation. In each case, the level presented is the one which has the highest number or the highest rank. It is also possible to present a plurality of levels next to one another simultaneously. If two levels cannot be presented in parallel, provision may be made for the level with the higher rank to cover the level with the lower rank.

The definition of levels allows the contents to be grouped within the calendar grid.

In one development of the method according to at least one embodiment of the invention, said method additionally comprises the following:
a new medical scheduling data item and an assigned data level association are detected,
the new scheduling data item and the assigned data level association are stored.

The further method steps described concern themselves with the process of including new scheduling data in the job planning or in a database which stores this information.

A user wishing to add and store a new scheduling data item normally selects the type which the new scheduling data item is intended to be. Selection of the type also stipulates the data level of the new scheduling data item.

One of the data levels may be defined as a base level which comprises a time frame.

The base level determines the basic contents of a calendar which is used as a basis for the job planning. The base level can take account of the selection of the appliances, the selection of the time window and the duration of individual slots in the calendar. The base level usually cannot be hidden, since the level defines the appointments and their reference. On this basis, the contents of the other levels can be displayed.

The data levels may have assigned priorities which control the display of the data levels. This allows contents which are appropriate to the task to be displayed for the user. The prioritization is a simple and comprehensible piece of logic. The prioritization allows compact presentation when there are several entries in one row in the calendar.

The selected data levels can be grouped into a level combination which a user can select in order to select the data levels grouped in the selected level combination jointly for display. Such defined compilation of level combinations which the user can access allows rapid changeover to the presentation of contents in a manner which is appropriate to the tasks. The user is provided with the option of compiling the levels himself when needed and of defining this compilation using a name of his own.

By introducing levels which relate to scheduling data, it is possible for tools which relate to the calendar to be grouped comprehensibly. The activities which need to be performed using the calendar can be grouped on the basis of the reference to the level. This results in consistent grouping with matching content.

In addition, the object based on the invention can also be achieved by a scheduling system. The scheduling system can be developed with the features of the method described above or in line with the subclaims.

An alternative solution provides a computer program product which is intended for storing the method described above.

BRIEF DESCRIPTION OF THE DRAWINGS

The detailed description of the figures which follows discusses example embodiments, which are to be understood to be nonlimiting, with their features and further advantages with reference to the drawing, in which.

DETAILED DESCRIPTION OF THE EXAMPLE EMBODIMENTS

Figure 1:
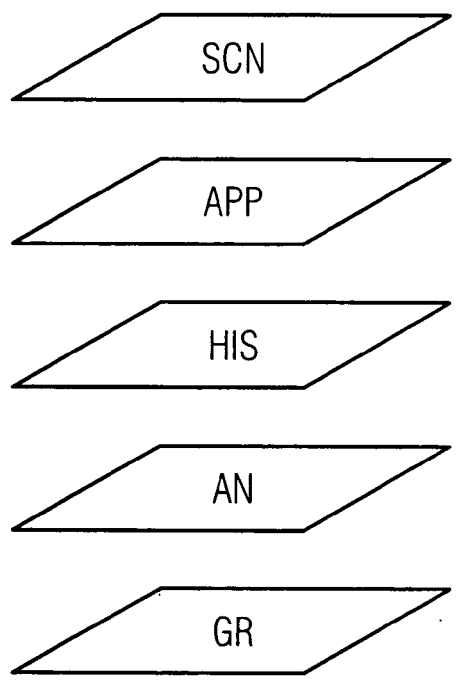
FIG. 1 shows different data levels and the arrangement thereof.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a few data levels which can be associated with scheduling data. From top to bottom, these are the levels "Scan" SCN, "Appointments" APP, "History (Cancellations)" HIS, "Annotations" AN and "Calendar Grid" GR.

The scan level SCN contains scheduling data, which reproduce the actual appointment situation on a medical appliance or a plurality of appliances. The scan level allows scheduled appointments to be compared and contrasted with the times of day at which the appointments were actually dealt with or carried out.

The appointments level APP shows the currently allocated appointments, which for their part relate to patients.

The level HIS contains the deleted/cancelled appointments. These also include those appointments for which the patient has not appeared or which the patient cancelled at the last minute. The level HIS allows deleted/cancelled appointments to be traced back, which is required in order to understand why the medical appliance was not operating. This level is not needed during normal routine use of the scheduling system, but rather is used primarily for retrospective analysis and optimization of operating cycles.

The level AN contains various information needed for scheduling. This may be free text annotations (for example: doctor 1 on holiday, doctor 2 not present, team meeting) or may relate to the examination planning (for example: colored marking yellow, green, with the option of assigning meanings to the colors: yellow: lumbar spine, green: head). The level AN can be covered by other levels, particularly by the appointments level APP. The information which the level AN contains can be used to coordinate the operation of the practice or radiological department more efficiently. One example mentioned may be the minimization of the conversion times for the appliances when the type of examination changes. In addition, the level AN helps to reduce the complexity of training for the personnel, since it covers numerous aspects of the operation of a practice/department and presents them to the personnel.

The base level GR determines the basic contents of the calendar.

The base level GR, the appointments level APP and the scan levels SCN can be displayed together.

Figure 2:
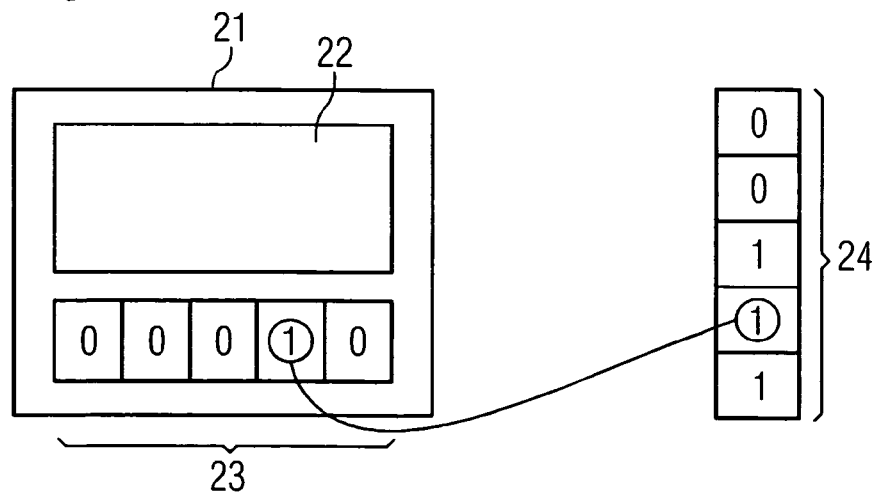
FIG. 2 shows an illustration of a scheduling data item as a data object, and a data object for the data levels which are currently to be displayed.

FIG. 2 shows a scheduling data item 21 illustrated as a data object. The scheduling data item 21 comprises a data field 22 for useful data and a data field 23 for the data level association information in the scheduling data item 21. The data level association information is illustrated as a bit array. The scheduling data item shown in FIG. 2 is associated with the fourth from a total of five data levels.

The right-hand side of FIG. 2 schematically shows a bit array 24 which indicates the data levels which are currently to be displayed. At present, three of the five data levels are to be displayed, including the data level which has the associated scheduling data item 21. For this data level, there is therefore a match between the bit arrays 23 and 24, which means that the scheduling data item 21 needs to be displayed in the situation shown.

Figure 3:
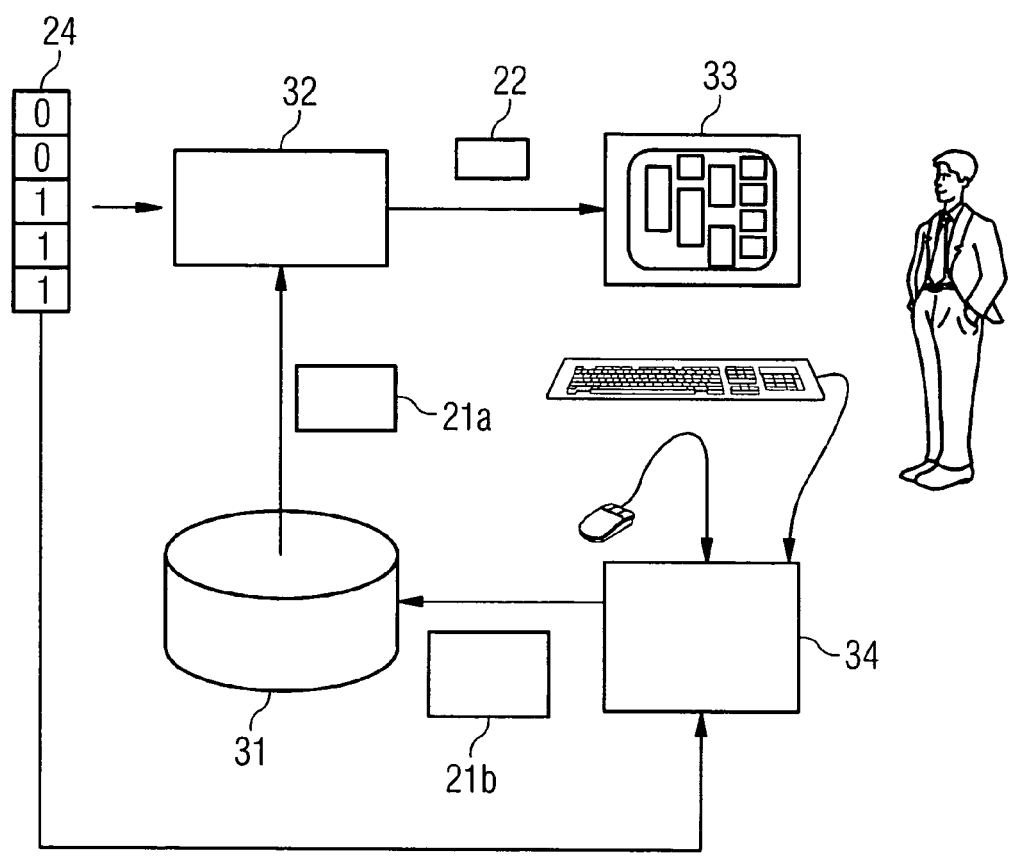
FIG. 3 shows a schematic illustration of the scheduling system with a few central elements.

FIG. 3 shows the scheduling system according to an embodiment of the invention as a block diagram. A view generator 32 is designed to receive a scheduling data item 21a which is to be displayed from a database 31. The view generator 32 compares the data field for data level association information in the scheduling data item 21a (see FIG. 2) with a bit array 24 which indicates the data levels which are currently to be displayed. If a data level matches in this case, the data field 22 for useful data in the scheduling data item 21a is conditioned by the view generator 32 for display on a screen 33 and is sent to the latter. A user can view the useful data in the scheduling data item on the screen.

To input a new scheduling data item, the user can use a keyboard, a mouse or another suitable data input device. To this end, the user can click on a button on the graphical user interface, for example, said button being linked to the action of creating a new scheduling data item of a particular type. The new entry is captured in a scheduling module 34, which checks the new entry for any conflicts with scheduling data which have already been entered. If the user is providing no different arrangements, the scheduling module 34 assumes that the scheduling data item 21b to be newly entered needs to be associated with the data level which corresponds to the scheduling data item's type chosen by the user. The data field for the data level association information in the scheduling data item 21b is initialized as appropriate, i.e. in the example case of a bit array, the bit which corresponds to the relevant data level is set to "1". Next, the scheduling data item 21b is sent to the database 31 and is stored therein.

Finally, it should be pointed out that the description of the example embodiments are to be understood, in principle, as nonlimiting in respect of a particular physical implementation of the invention. In particular, it is obvious to a person skilled in the relevant art that the invention can be implemented partly or completely in software and/or hardware and/or in a form distributed over a plurality of physical products—in this case particularly also computer program products.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating a medical scheduling system for processing and displaying medical scheduling data which relate to job planning for a medical appliance and of which each scheduling data item is associated with a data level, the method comprising:
    determining a bit array representing a data level associated with a respective scheduling data item to be displayed from an electronic database, the data level being one of a plurality of data levels, each of the plurality of data levels being associated with one of a plurality of scheduling functions of the medical appliance and the data level association relates to the data level associated with the scheduling data item;
    selectively ascertaining at least one data level from the plurality of data levels to be displayed;
    determining actual sequences of appointments for use of the medical appliance based on a minimization of conversion times for the medical appliance when the type of examination changes;
    comparing, using a view generator, the actual sequences of appointments for use with scheduled appointments for the use of the medical appliance;
    comparing the data level association of the scheduling data item to be displayed with the at least one data level which is currently to be displayed;
    displaying the scheduling data item to be displayed together with the result of the comparison between the actual usage and the scheduling data item on a display if the data level association corresponds to at least one data level which is currently to be displayed; and
    displaying a level combination of selected data levels upon user selection of a plurality of data levels for joint display.

2. The method as claimed in claim 1, further comprising:
    detecting a new medical scheduling data item and an assigned data level association; and
    storing the new scheduling data item and the assigned data level association.

3. The method as claimed in claim 2, wherein one of the data levels is defined as a base level which includes a time frame.

4. The method as claimed in claim 2, wherein the data levels have assigned priorities which control the display of the data levels.

5. The method as claimed in claim 2, wherein selected data levels are grouped into a level combination which a user can select in order to select the data levels grouped in the selected level combination jointly for display.

6. The method as claimed in claim 1, wherein one of the data levels is defined as a base level which includes a time frame.

7. The method as claimed in claim 1, wherein the data levels have assigned priorities which control the display of the data levels.

8. The method as claimed in claim 1, wherein selected data levels are grouped into a level combination which a user can select in order to select the data levels grouped in the selected level combination jointly for display.

9. The method as claimed in claim 1, wherein the data levels include a medical appliance scheduling data level, a patient appointment data level, a patient appointment history data level, an annotations data level, and a calendar grid data level.

10. The method as claimed in claim 1, wherein displaying the data levels includes displaying different data levels simultaneously and displaying all relevant medical scheduling data in a single view for different medical appliances.

11. A medical scheduling system for the job planning for a medical appliance, comprising:
    a view generator configured to produce a compilation of information which is to be presented, wherein
        the view generator includes an input interface for a level selection information item and the information to be presented is associated with at least one data level,
        the view generator is configured to determine actual sequences of appointments for use of the medical appliance based on a minimization of conversion times for the medical appliance when the type of examination changes;
        the view generator is configured to compare the actual sequences of appointments for use with the scheduled appointments for the use of the medical appliance;
        the view generator is configured to include in the compilation the result of the comparison between the actual usage and the scheduling data item and-information which corresponds to at least one data level which is currently to be displayed, each of the at least one data levels being associated with one of a plurality of scheduling functions of the medical appliance, and the view generator is configured to displaying a level combination of selected data levels upon user selection of a plurality of data levels for joint display.

12. The scheduling system as claimed in claim 11, further comprising:
a scheduling module, designed to detect a new medical scheduling data item and an associated data level association, wherein the scheduling module is designed to store the new scheduling data item and the assigned data level association.

13. The scheduling system as claimed in claim 12, wherein one of the data levels is defined as a base level which includes a time frame.

14. The scheduling system as claimed in claim 11, wherein one of the data levels is defined as a base level which includes a time frame.

15. The scheduling system as claimed in claim 11, wherein the data levels have assigned priorities which control the display of the data levels.

16. The scheduling system as claimed in claim 12, wherein the data levels have assigned priorities which control the display of the data levels.

17. A non-transitory computer readable medium comprising:
program segments for processing medical scheduling data which relate to the job planning for a medical appliance and of which each scheduling data item is associated with a data level, when the program segments are executed on a computer device, causing the computer device to perform the following steps,
determining a data level association for each scheduling data item to be displayed, the data level being one of a plurality of data levels, each of the plurality of data levels being associated with one of a plurality of scheduling functions of the medical appliance and the data level association relates to the data level associated with the scheduling data item,
selectively ascertaining the at least one data level currently to be displayed,
determining actual sequences of appointments for use of the medical appliance based on a minimization of conversion times for the medical appliance when the type of examination changes;
comparing the actual sequences of appointments for use with the scheduled appointments for the use of the medical appliance;
comparing the data level association of the scheduling data item to be displayed with the at least one data level which is currently to be displayed;
displaying the scheduling data item to be displayed together with the result of the comparison between the actual usage and the scheduling data item if the data level association corresponds to at least one data level which is currently to be displayed; and
displaying a level combination of selected data levels upon user selection of a plurality of data levels for joint display.

18. The method as claimed in claim 17, wherein one of the data levels is defined as a base level which includes a time frame.

19. The method as claimed in claim 17, wherein the data levels have assigned priorities which control the display of the data levels.

20. The method as claimed in claim 17, wherein selected data levels are grouped into a level combination which a user can select in order to select the data levels grouped in the selected level combination jointly for display.

* * * * *